United States Patent
Boebel et al.

[11] Patent Number: 6,063,096
[45] Date of Patent: May 16, 2000

[54] NEEDLE HOLDER

[75] Inventors: Manfred Boebel, Oetisheim; Andreas Dingler, Birkenfeld; Johann Sarbu, Achim, all of Germany

[73] Assignee: Richard Wolf GmbH, Knittlingen, Germany

[21] Appl. No.: 09/041,530

[22] Filed: Mar. 12, 1998

[30]    Foreign Application Priority Data

Mar. 13, 1997 [DE] Germany .......................... 197 10 432

[51] Int. Cl.[7] .................................................. A61B 17/00
[52] U.S. Cl. ............................................................ 606/148
[58] Field of Search ................................. 606/148, 147, 606/144, 139, 145; 112/169, 80.03

[56]    References Cited

U.S. PATENT DOCUMENTS 5,250,126  10/1993  Filipi et al. .............................. 606/144
5,522,820   6/1996  Caspari et al. .......................... 606/148

FOREIGN PATENT DOCUMENTS 0 437 063 B1   7/1996   European Pat. Off. .
41 27 812 C 2  9/1996   Germany .

Primary Examiner—Michael Buiz
Assistant Examiner—Vikki Trinh
Attorney, Agent, or Firm—Cohen, Pontani, Lieberman & Pavane

[57]    ABSTRACT

The endoscopic instrument is formed as a needle holder with ligature scissors. It comprises at its distal end a jaw-like tool and at its proximal end a handle, these being connected to one another by a common shank. At the distal tool end there is formed the ligature holder and the ligature scissors proximally neighboring thereto. Between these tool parts there is formed a projection limiting the free passage between the needle holder and the ligature scissors, this projection being dimensioned such that although the ligature may be guided through, the needle however cannot get into the region of the scissors.

7 Claims, 3 Drawing Sheets

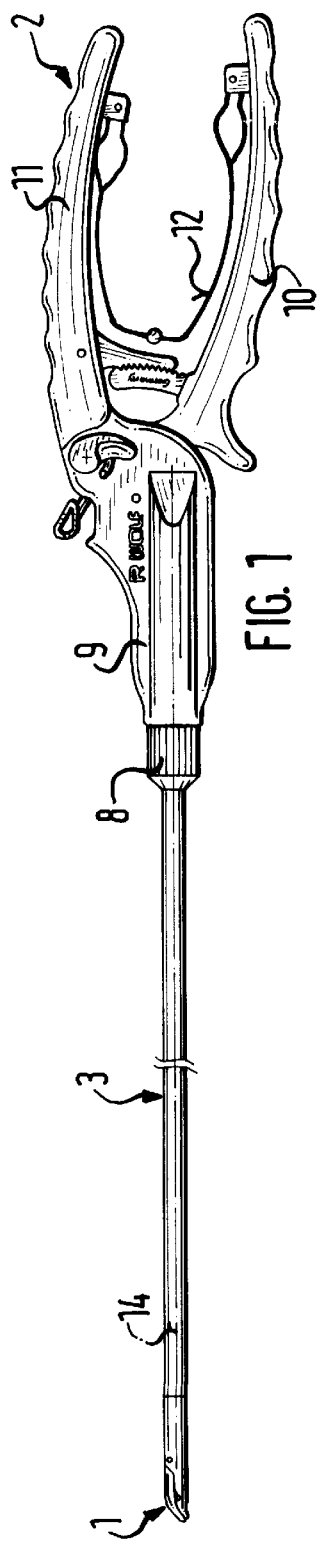
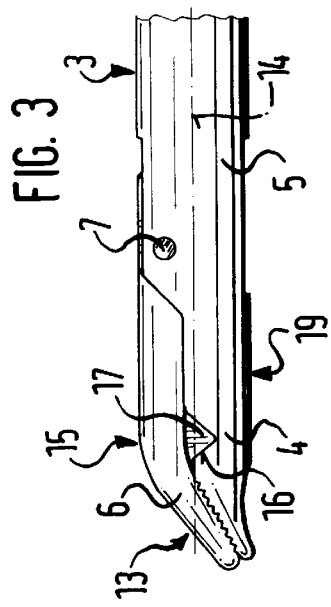
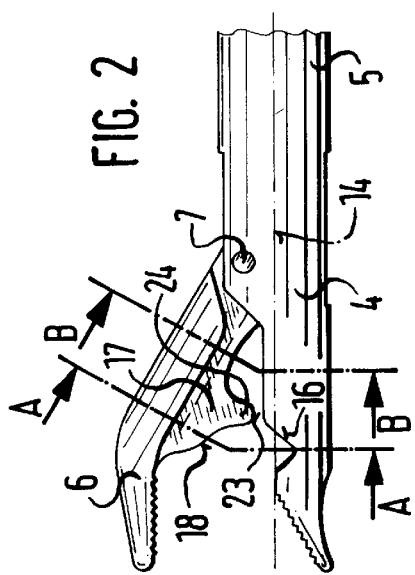
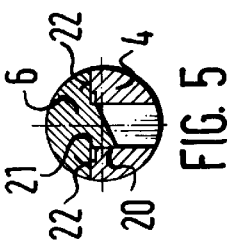

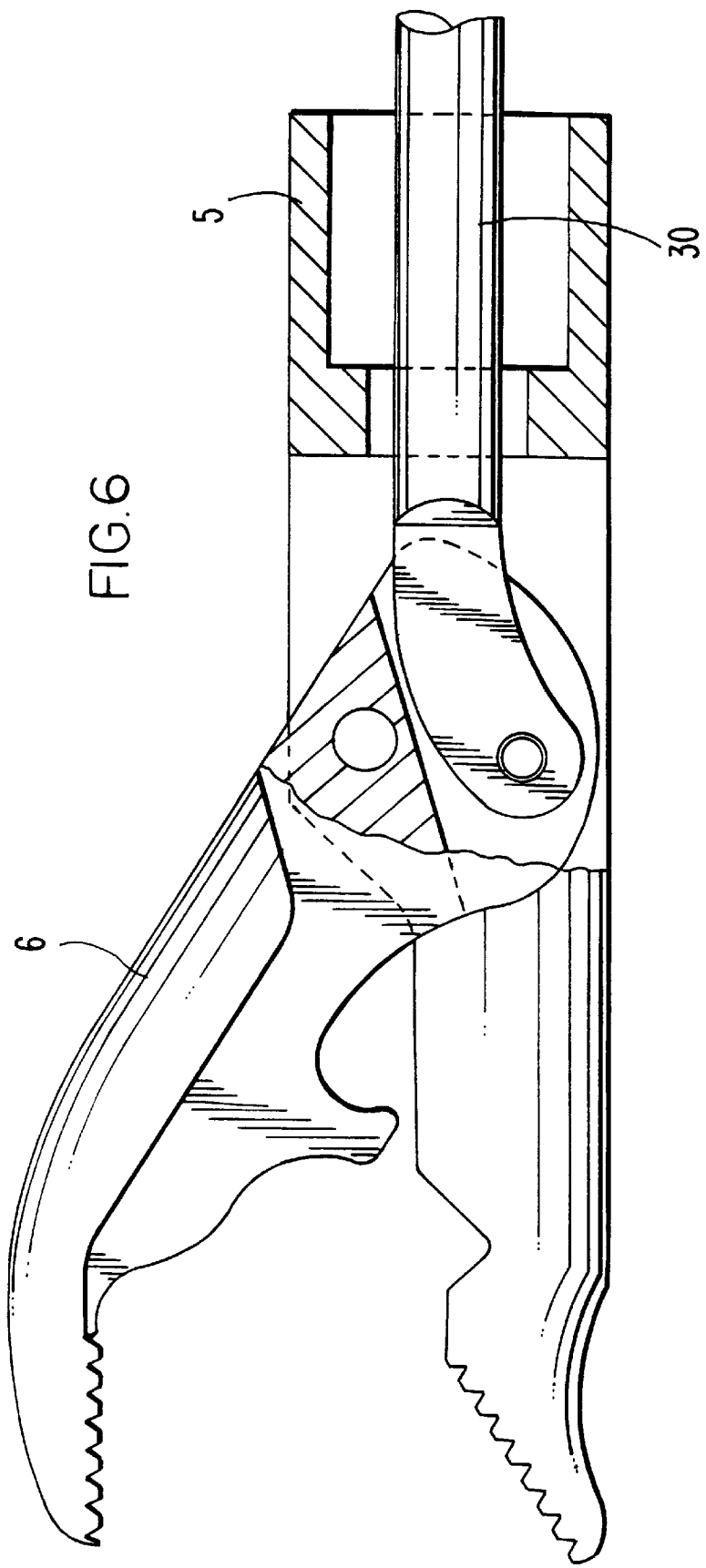

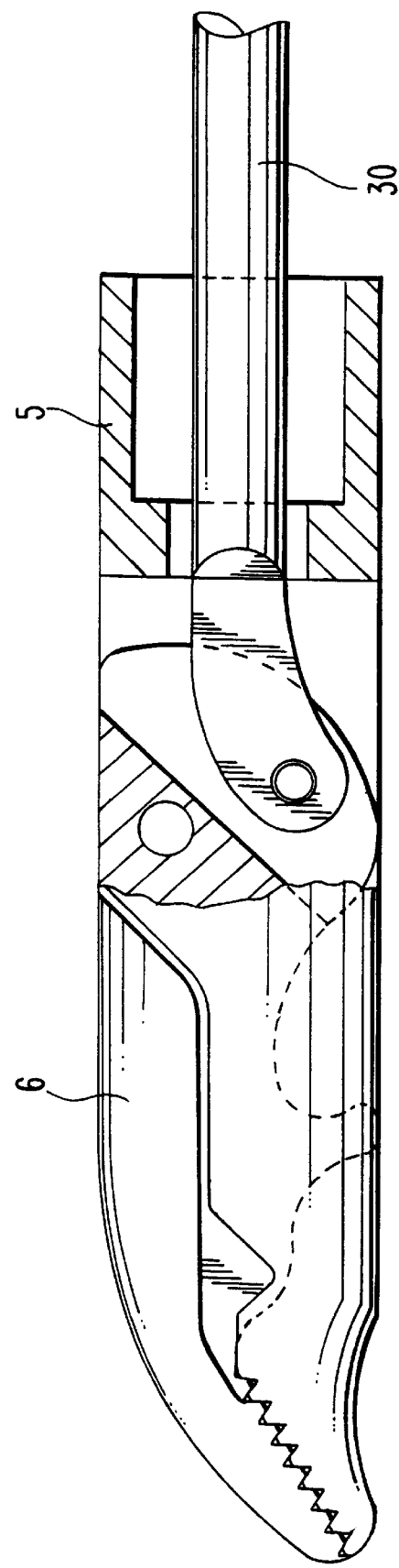

NEEDLE HOLDER

BACKGROUND OF THE INVENTION

The invention relates to a needle holder with ligature scissors.

Needle holders especially for endoscopic operations are known in the art. In DE 41 27 812 C2 there is described a needle holder with a forceps-shaped tool part and a scissor grip type handle part. From EP 0 437 063 B1 there is known a needle holder which additional to the actual holding function also automatically effects an alignment of the needle in a defined position, thus apart from the holding function it fulfills also a positioning function, which in particular with the use of curved needles not only carries out a defined positioning transversely to the instrument axis, but also a defined positioning of the curve arrangement to the instrument axis. Although the needle holder described in this document is favorably designed with repect to its positioning characteristic, it is not with regard to the tool arrangement, since the needle for the purpose of gripping is to be inserted into a tube relief. Thus with this needle holder one can only operate close to the object in a limited manner, which in practice entails certain disadvantages. Also this needle holder can only be used for holding needles, other gripping procedures such as can be effected with the needle holder known from DE 41 27 812 C2 may thus not be carried out due to design restrictions.

Different from open operations, with endoscopic operations a change of instrument is often complicated, in particular when the body cavity in which the operation is carried out is subject to pressure means. With this aspect in mind a needle holder offered by the company Lawton medical technology represents an improvement in which the needle holder is combined with a ligature scissors. Such a combined instrument is principly advantageous since at least on setting the individual head stitches after forming the knot the ligature must be cut in order to set a further individual head stitch.

In practice however problems may arise when the needle is not grasped as intended with the needle holder located at the distal end, but a piece slips further proximally and gets into the region of the ligature scissors. Since the lever effect in the region of the scissors is usually larger than in the region of the holder, this slipping of the needle or of the needle holder leads regularly to lasting damage on at least one blade of the ligature scissors. With lasting damage however as a rule even during the operation the instrument must be exchanged, since otherwise a severing of the ligature is not possible. In any case a subsequent grinding or even the replacement of the tool is necessary, which is complicated and expensive.

BRIEF SUMMARY OF THE INVENTION

Against this state of the art it is the object of the invention, preceding from the last mentioned state of the art, to so improve a combined instrument of the known type that the previously mentioned disadvantages are avoided and an instrument is provided with which the needle can be reliably held and the ligature reliably severed, without there arising the danger of damage to the blade by the needle. In a further development of the invention furthermore a simple and reliable alignment, in particular of curved needles, is to be possible and the instrument is to be useful for other types of gripping procedures. Furthermore the instrument is to be simple to operate and to clean.

Accordingly the invention provides that on at least one arm of the scissors there is provided a projection which is aligned towards the other tool arm and which limits the free passage from the needle holder to the ligature scissors. This projection ensures that on gripping the needle this does not inadvertently get into the cutting region of the scissors. With this in a simple embodiment the projection may be designed such that on guiding the instrument in the direction of its longitudinal axis, a needle reaching into the tool comes to rest on this projection and does not reach up into the cutting region. Preferably however the projection is so dimensioned that the remaining free space between this projection and the oppositely lying arm, even with a completely opened tool jaw, has a slight width which is the same or is larger that the width of the employed ligature, but is however smaller than thickness of the needle located therein. In this manner it is securely ruled out that the needle gets into the region of the ligature scissors. It is understood that the latter embodiment variation only functions with the use of directed needle ligature combinations which fulfill the previously mentioned conditions with regard the thickness of the ligature and needle.

It is advantageous when the part of the tool forming the needle holder comprises a flat forceps-like part provided at the distal instrument end as well as a positioning and holding part connecting proximally thereto. This flat forceps-like part permits the gripping of not only the needle and ligature, but also where appropriate other objects and thus avoids in particular the disadvantages outlined earlier which result with the needle holder known from EP 0 437 063 B1. One may operate at practically any vicinity to the object with this forceps part. With this instrument therefore, apart from holding and guiding the needle and ligature, also other gripping operations may be exercised, which is particularly advantageous with endoscopic instruments with which a change of instrument is relatively drawn out and complicated.

Whilst the forceps part is suitable for holding the needle as well as for gripping and holding other objects, the positioning and holding part proximally connecting thereto is provided exclusively for holding and positioning a needle. This positioning function is in particular quite advantageous with curved needles since the needle on closing the jaw part is automatically brought into a defined position independently of the position from which it has been gripped. This positioning and holding part is preferably located between the forceps part and the ligature scissors, wherein the projection limiting the passage between the needle holder and ligature scissors is arranged in the region between the positioning and holding part and the ligature scissors.

The shank of the instrument is preferably formed by a tube which reaches up to the distal instrument end and here is formed as a stationary arm of the tool. The further arm may then be pivotably mounted near to the distal end within the tube, wherein the operation may be effected by a rod guided within the tube so that compression as well as tension forces may be transmitted, which likewise with regard to the handling is advantageous, since the jaw-like tool may then be used for expanding. Such a tubular shank with an operating rod guided therein is furthermore easy to clean. For forming the tool arm the distal tube end is recessed approximately halfway (with respect to the longitudinal middle axis), so that in this region a roughly U-shaped cross section of a comparatively short arm length arises which is then formed running out flatly towards the gripping surface of the forceps part.

The projection limiting the passage to the ligature scissors is advantageously led further up to into the region of the positioning and holding part so that here it represents part of an at least three point bearing which serves for holding and positioning the needle. The positioning secureness and the holding function may still be further improved when the tube which is halved in this region is laterally recessed V-shaped so that there results a five point bearing in this region of which four points are formed by the halved, here laterally V-shaped recessed tube and the fifth point by the projection. The pivotingly moving arm comprising the projection then holds the needle in its position or guides this needle on closing the jaw part in the defined position as directed.

A fouling between the ligature scissors and needle may then, as elaborated above, only be reliably prevented when directed needle ligature combinations are employed, these in their thickness dimensions being adapted to the instrument or vice versa. If however which in practice cannot always be avoided, non-directed needle and ligature combinations, in particular such with small thickness dimensions are employed, then it is useful when on the instrument also in the region of the ligature scissors precautions are taken which keep the damage resulting from fouling between the needle and scissors as small as possible. For this the invention provides for the blade which is arranged on the stationary tool part to be arranged displaced underneath with respect to lateral bearing surfaces, so that a needle reaching here or other object may not come into contact at least with this lower blade formed from one piece with the tube. Although with this a damaging of the opposite counter blade cannot be excluded, this component mounted pivotingly moving can be exchanged and is considerably easier to subsequently grind than the counter blade which is formed from one piece with tube.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims.

BRIEF DESCRIPTION OF THE DRAWINGS

The invention is hereinafter described in more detail by way of an embodiment example shown in the drawings. There are shown:

FIG. 1 a view of the instrument according to the invention in a simplified representation;

FIG. 2 the distal instrument part in an enlarged representation according to FIG. 1 with an opened jaw part;

FIG. 3 the distal instrument part in an enlarged representation according to FIG. 1 with a closed jaw part;

FIG. 4 a section taken along the section line A—A in FIG. 2 and

FIG. 5 a section taken along the section line B—B in FIG. 2;

FIG. 6 is a longitudinal section of FIG. 2; and

FIG. 7 is a longitudinal section of FIG. 3.

DETAILED DESCRIPTION OF THE INVENTION

As can be seen from FIG. 1, the instrument consists essentially of a tool 1 arranged on the distal side, a handle 2 arranged on the proximal side and a shank 3 connecting these. The tool 1 is formed two-armed and comprises a lower stationary arm 4 which is formed from one piece with a tube 5 which forms the shank 3. An upper arm 6 is mounted pivotingly movable in the distal end region of the tube 5, the pivoting axis which is formed pin-shaped is indicated at 7. The upper arm 6 is extended beyond the pivoting axis 7 and here is linked on a rod 30 which is guided within the tube 5 in a longitudinally displaceable manner (as seen in FIG. 6).

The tube is releasably fixed on a housing 9 by way of a cap 8 which forms the stationary part of the handle 2. Within this housing a hand grip 10 is pivotably mounted. The oppositely lying hand grip 11 is part of the housing 9 and is stationary. Between the hand grips 10 and 11 there is provided a spring 12 as well as a latching means not to be described in any detail here which can be set out of function. The rod 30 guided within the tube 5 is linkedly connected to the end of the hand grip 10 lying within the housing 9 in such a manner that on moving the hand grips 10 and 11 towards one another the jaw part on the distal side formed from arms 4 and 6 are guided from the open position shown in FIG. 2 into the closed position shown in FIG. 3.

The tool 1 formed from the arms 4 and 6 is membered essentially in three parts. The distal end is formed by a forceps part 13. This forceps part 13 is designed in the manner of a flat forceps, the arms 4 and 6 pivotable towards one another are formed essentially flat in this region and equipped on both arms with linear elevations running transversely to the longitudinal axis 14 of the instrument, which engage into one another in the manner of a toothing (see FIG. 3). To this forceps part in the proximal direction there is connected a holding and positioning part 15. Whilst the forceps part 13 may serve the gripping and holding of practically any object, the positioning and holding part 15 is provided exclusively for holding and positioning the needle. In this region the lower arm 4 is provided with V-shaped recesses 16 in the lateral arms, the recesses running taperingly downwards. The upper arm 6 comprises in this region a roughly middle arranged projection 17 facing towards the lower arm 4, the projection being arranged and designed such that on closing the jaw part it may be integrated between the sides of the lower arm 4. The side 18 of this projection, facing distally downwards, forms a bearing surface for positioning and holding the needle being accommodated in the V-shaped recesses 16.

If then a curved needle is guided into the region of these V-shaped recesses, then on closing the jaw part the side 18 of the projection 17 turns this needle such that the projection 17 reaches as far as possible towards the lower arm 4 which causes the needle to turn in such a manner that its ends and thus also its tip faces upwards with respect to the representation according to FIG. 1. Apart from this positioning effect this arrangement still further has the advantage that the needle must only partly by holding force be fixed into this position, since the needle is at least partly held with a positive fit.

A ligature scissors 19 connects proximally to the positioning and holding part 15. A blade 20 (FIG. 5) of this scissors 19 is formed by an extension of the projection 17. The counter blade 21 is formed by the stationary lower arm 4, this being by the inner side of the left arm in the cross sectional representation according to FIG. 5, of the U-shaped tube section which in this region is formed open on the web side. The counter blade 21 is, as can be seen from FIG. 5, formed downwardly displaced with respect to lateral bearing surfaces 22. This downwardly displaced arrangement of the counter blade 21 prevents an object which reaches the cutting region from damaging the counter blade 21 which is difficult to repair. Such an object comes to rest on the bearing surfaces 22 and thus at a safe distance in front of the counter blade 21. If on the other hand a ligature is guided into this region then on closing of the jaw part it is pulled by the blade 20 to the counter blade 21 and is cut on this. In order to prevent objects in particular the needle to be handled, from getting into the region of the ligature scissors 19, the projection 17 is so designed in the region between the positioning and holding part 15 and the ligature scissors 19, that with a completely opened jaw part (FIG. 2), it limits the passage 23 to the ligature scissors 19 in such a manner that on application of a correspondingly dimensioned needle ligature combination, although the ligature may be guided through this passage 23 to the ligature scissors 19, not however the needle. This passage 23 is limited by the end 24 of the projection 17, facing the arm 4, in combination with the lower arm 4.

At the proximal end of the shank 3 there is provided a tubing connection piece (not shown) which permits the rinsing through of the shank and thus a lasting cleaning.

We claim:

1. A needle holding instrument for endoscopic operations, comprising:

a shank having a proximal end and a distal end;

a handle connected to said proximal end of said shank; and a tool connected to said distal end of said shank, said tool comprising at least two arms, said at least two arms being movable relative to each other between a first and a second position, wherein one of said at least two arms comprises a needle holder, and another one of said at least two arms comprises ligature scissors, wherein one of said at least two arms comprises a projection, oriented to face another one of said at least two arms, for limiting free passage between said needle holder and said ligature scissors said needle holder comprising a flat forceps part, said flat forceps part forming a distal instrument end, and a positioning and holding part proximately connected thereto, said projection being positioned between said positioning and holding part and said ligature scissors.

2. The needle holding instrument of claim 1, wherein said projection is dimensioned such that when said arms are moved to said first position and a needle connected to a ligature is used in conjunction with the needle holding instrument, said projection restricts passage of the needle from said needle holder to said ligature scissors but enables passage of the ligature therethrough.

3. The needle holding instrument of claim 2, wherein one of said at least two arms is stationary with respect to said other one of said at least two arms, and wherein said shank comprises a tube extending to said distal instrument end such that said stationary arm comprises a portion of said tube at said distal instrument end.

4. The needle holding instrument of claim 3, wherein one of said at least one arms is pivotably mounted on said distal shank end, further comprising an operating member having a first side and a second side, said member being guidably disposed within said shank, wherein said first side of said operating member is connected to said handle and said second side of said operating member is connected to said pivotably mounted arm.

5. The needle holding instrument of claim 4, comprising at least three bearing points for a needle, wherein said projection extends to said positioning and holding part such that one of said at least three bearing points is defined at said positioning and holding part, and wherein said tube comprises an open region where said tube is substantially halved forming lateral bearing surfaces such that said lateral bearing surfaces define other ones of said at least three bearing points.

6. The needle holding instrument of claim 5, wherein said ligature scissors comprise a blade positioned on one of said at least two arms and a counter-blade on the other of said at least two arms, wherein one of said blade and counter blade that is positioned on said stationary arm is recessed relative to said lateral bearing surfaces.

7. The needle holding instrument of claim 6, wherein one of said at least two arms comprises said positioning and holding part, wherein said positioning and holding part comprises lateral parts formed by said tube in said open region, and wherein each of said lateral parts comprises a laterally positioned V-shaped recess open towards another one of said at least two arms.

\* \* \* \* \*